United States Patent
Tomita et al.

(10) Patent No.: US 10,422,548 B2
(45) Date of Patent: Sep. 24, 2019

(54) AIR-CONDITIONING APPARATUS WITH OPERABILITY BASED ON FLAMMABLE REFRIGERANT CONCENTRATION INFORMATION IN OUTDOOR UNIT

(71) Applicant: Mitsubishi Electric Corporation, Tokyo (JP)

(72) Inventors: Masafumi Tomita, Tokyo (JP); Yasuhiro Suzuki, Tokyo (JP); Masahiro Takamura, Tokyo (JP); Katsuyuki Amano, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 419 days.

(21) Appl. No.: 15/109,152

(22) PCT Filed: Dec. 15, 2014

(86) PCT No.: PCT/JP2014/083147
§ 371 (c)(1),
(2) Date: Jun. 30, 2016

(87) PCT Pub. No.: WO2015/133036
PCT Pub. Date: Sep. 11, 2015

(65) Prior Publication Data
US 2016/0327303 A1      Nov. 10, 2016

(30) Foreign Application Priority Data

Mar. 3, 2014   (JP) .................. 2014-040624

(51) Int. Cl.
*F24F 11/89*    (2018.01)
*F25B 13/00*    (2006.01)
(Continued)

(52) U.S. Cl.
CPC .............. *F24F 11/89* (2018.01); *F24F 11/30* (2018.01); *F24F 11/62* (2018.01); *F25B 13/00* (2013.01);
(Continued)

(58) Field of Classification Search
CPC ...... F24F 11/02; F24F 11/0009; F24F 11/006; F24F 2011/0063; F25B 49/005; F25B 2500/24; F25B 2400/12; F25B 2500/23
See application file for complete search history.

(56) References Cited

U.S. PATENT DOCUMENTS 4,261,847 A * 4/1981 Cooper ................. C09K 5/045
                                                           252/67
5,660,051 A * 8/1997 Sakakibara ........ B60H 1/00764
                                                           62/114
(Continued)

FOREIGN PATENT DOCUMENTS

CN    202119019 U  *  1/2012
CN    102954614 A     3/2013
(Continued)

OTHER PUBLICATIONS

Office Action dated May 19, 2017 issued in corresponding CN application No. 201510089237.6 (and English translation).
(Continued)

*Primary Examiner* — Nelson J Nieves
(74) *Attorney, Agent, or Firm* — POSZ Law Group, PLC

(57) ABSTRACT

An air-conditioning apparatus determines whether or not to permit an air-conditioning operation based on refrigerant amount information stored in an outdoor unit and installation height information stored in an indoor unit.

11 Claims, 10 Drawing Sheets

(51) Int. Cl.
    *F25B 49/00*     (2006.01)
    *G01N 25/50*     (2006.01)
    *F24F 11/30*     (2018.01)
    *F24F 11/62*     (2018.01)
    *F24F 140/12*    (2018.01)
    *F24F 11/64*     (2018.01)

(52) U.S. Cl.
    CPC ........... *F25B 49/005* (2013.01); *G01N 25/50* (2013.01); *F24F 11/64* (2018.01); *F24F 2140/12* (2018.01); *F25B 2400/12* (2013.01); *F25B 2500/23* (2013.01); *F25B 2500/24* (2013.01)

(56) References Cited

U.S. PATENT DOCUMENTS

| | | | | |
|---|---|---|---|---|
| 6,073,455 | A * | 6/2000 | Tachigori | F25B 49/005 62/129 |
| 6,644,047 | B2 * | 11/2003 | Taira | F25B 49/005 62/129 |
| 9,760,796 | B2 * | 9/2017 | Manabe | F24F 11/30 |
| 2002/0178738 | A1 * | 12/2002 | Taira | F25B 49/005 62/129 |
| 2007/0204635 | A1 * | 9/2007 | Tanaka | F25B 13/00 62/129 |
| 2009/0019872 | A1 * | 1/2009 | Kotani | F25B 41/062 62/225 |
| 2011/0000234 | A1 * | 1/2011 | Nishimura | F25B 49/005 62/77 |
| 2011/0108756 | A1 * | 5/2011 | Tsuchiya | C09K 5/045 252/68 |
| 2013/0213068 | A1 * | 8/2013 | Goel | F25B 49/005 62/129 |
| 2014/0223941 | A1 * | 8/2014 | Nishimura | F25B 49/02 62/190 |
| 2016/0012309 | A1 * | 1/2016 | Manabe | F24F 11/30 700/276 |

FOREIGN PATENT DOCUMENTS

| | | |
|---|---|---|
| EP | 2559959 A2 | 2/2013 |
| JP | H10-038354 A | 2/1998 |
| JP | 2002-372317 A | 12/2002 |
| JP | 2013-040730 A | 2/2013 |

OTHER PUBLICATIONS

Office Action dated Aug. 23, 2016 for the corresponding JP application No. 2014-040624 (and English translation).
International Search Report of the International Searching Authority dated Mar. 10, 2015 for the corresponding International application No. PCT/JP2014/083147 (and English translation).
Extended EP Search Report dated Oct. 5, 2017 issued in corresponding EP patent application No. 14884764.3.

* cited by examiner

FIG. 3

| INFORMATION | TYPE |
|---|---|
| 1 | CEILING TYPE (2.2 m) |
| 2 | WALL TYPE (1.8 m) |
| 3 | WINDOW TYPE (1.0 m) |
| 4 | FLOOR TYPE (0.6 m) |

FIG. 4

| OUTDOOR UNIT INFORMATION | INDOOR UNIT INFORMATION | PERMIT OPERATION OR NOT |
|---|---|---|
| 1 (REFRIGERANT AMOUNT: LARGEST) | 1 (CEILING) | PERMIT |
| | 2 (WALL) | NOT PERMIT (INHIBIT OPERATION) |
| | 3 (WINDOW) | NOT PERMIT (INHIBIT OPERATION) |
| | 4 (FLOOR) | NOT PERMIT (INHIBIT OPERATION) |
| 2 (REFRIGERANT AMOUNT: LARGE) | 1 (CEILING) | PERMIT |
| | 2 (WALL) | PERMIT |
| | 3 (WINDOW) | NOT PERMIT (INHIBIT OPERATION) |
| | 4 (FLOOR) | NOT PERMIT (INHIBIT OPERATION) |
| 3 (REFRIGERANT AMOUNT: MEDIUM) | 1 (CEILING) | PERMIT |
| | 2 (WALL) | PERMIT |
| | 3 (WINDOW) | PERMIT |
| | 4 (FLOOR) | NOT PERMIT (INHIBIT OPERATION) |
| 4 (REFRIGERANT AMOUNT: SMALL) | 1 (CEILING) | PERMIT |
| | 2 (WALL) | PERMIT |
| | 3 (WINDOW) | PERMIT |
| | 4 (FLOOR) | PERMIT |

FIG. 5

| INFORMATION | TYPE |
|---|---|
| 1 | CEILING TYPE (2.2 m) |
|   | WALL TYPE (1.8 m) |
| 2 | WINDOW TYPE (1.0 m) |
|   | FLOOR TYPE (0.6 m) |

FIG. 6

| OUTDOOR UNIT INFORMATION | INDOOR UNIT INFORMATION | PERMIT OPERATION OR NOT |
|---|---|---|
| 1 (REFRIGERANT AMOUNT: LARGE) | 1 (CEILING OR WALL) | PERMIT |
|   | 2 (WINDOW OR FLOOR) | NOT PERMIT (INHIBIT OPERATION) |
| 2 (REFRIGERANT AMOUNT: SMALL) | 1 (CEILING OR WALL) | PERMIT |
|   | 2 (WINDOW OR FLOOR) | PERMIT |

FIG. 7

| INFORMATION | TYPE |
|---|---|
| 1 | CEILING TYPE (2.2 m) |
| 1 | WALL TYPE (1.8 m) |
| 2 | WINDOW TYPE (1.0 m) |
| 3 | FLOOR TYPE (0.6 m) |

FIG. 8

| OUTDOOR UNIT INFORMATION | INDOOR UNIT INFORMATION | PERMIT OPERATION OR NOT |
|---|---|---|
| 1 (REFRIGERANT AMOUNT: LARGEST) | 1 (CEILING OR WALL) | PERMIT |
| 1 (REFRIGERANT AMOUNT: LARGEST) | 2 (WINDOW) | NOT PERMIT (INHIBIT OPERATION) |
| 1 (REFRIGERANT AMOUNT: LARGEST) | 3 (FLOOR) | NOT PERMIT (INHIBIT OPERATION) |
| 2 (REFRIGERANT AMOUNT: LARGE) | 1 (CEILING OR WALL) | PERMIT |
| 2 (REFRIGERANT AMOUNT: LARGE) | 2 (WINDOW) | PERMIT |
| 2 (REFRIGERANT AMOUNT: LARGE) | 3 (FLOOR) | NOT PERMIT (INHIBIT OPERATION) |
| 3 (REFRIGERANT AMOUNT: SMALL) | 1 (CEILING OR WALL) | PERMIT |
| 3 (REFRIGERANT AMOUNT: SMALL) | 2 (WINDOW) | PERMIT |
| 3 (REFRIGERANT AMOUNT: SMALL) | 3 (FLOOR) | PERMIT |

FIG. 9

| INFORMATION | TYPE |
|---|---|
| 1 | CEILING TYPE (2.2 m) |
| 2 | WALL TYPE (1.8 m) |
| 3 | WINDOW TYPE (1.0 m) |
|   | FLOOR TYPE (0.6 m) |

FIG. 10

| OUTDOOR UNIT INFORMATION | INDOOR UNIT INFORMATION | PERMIT OPERATION OR NOT |
|---|---|---|
| 1 (REFRIGERANT AMOUNT: LARGEST) | 1 (CEILING) | PERMIT |
|  | 2 (WALL) | NOT PERMIT (INHIBIT OPERATION) |
|  | 3 (WINDOW OR FLOOR) | NOT PERMIT (INHIBIT OPERATION) |
| 2 (REFRIGERANT AMOUNT: LARGE) | 1 (CEILING) | PERMIT |
|  | 2 (WALL) | PERMIT |
|  | 3 (WINDOW OR FLOOR) | NOT PERMIT (INHIBIT OPERATION) |
| 3 (REFRIGERANT AMOUNT: SMALL) | 1 (CEILING) | PERMIT |
|  | 2 (WALL) | PERMIT |
|  | 3 (WINDOW OR FLOOR) | PERMIT |

AIR-CONDITIONING APPARATUS WITH OPERABILITY BASED ON FLAMMABLE REFRIGERANT CONCENTRATION INFORMATION IN OUTDOOR UNIT

CROSS REFERENCE TO RELATED APPLICATIONS

This application is a U.S. national stage application of PCT/JP2014/083147 filed on Dec. 15, 2014, which claims priority to Japanese Patent Application No. 2014-040624 filed on Mar. 3, 2014, the contents of which are incorporated herein by reference.

TECHNICAL FIELD

The present invention relates to a separate-type air-conditioning apparatus using flammable refrigerant, and particularly, to an air-conditioning apparatus configured to have assured safety.

BACKGROUND ART

There is a conventional air-conditioning apparatus that performs refrigeration cycle by using an "HFC refrigerant" such as nonflammable R410A. Unlike an "HCFC refrigerant" such as conventionally used R22, this R410A has zero ozone depletion potential (hereinafter referred to as an "ODP"), and thus, does not damage the ozone layer, but has a high global warming potential (hereinafter referred to as a "GWP"). Thus, as a part of prevention of global warming, it has been investigated to shift from an HFC refrigerant having a high GWP, such as R410A, to a refrigerant having a low GWP (hereinafter referred to as a low-GWP refrigerant).

Candidates for a low-GWP refrigerant include an HC refrigerant such as R290 ($C_3H_8$: propane) and R1270 ($C_3H_6$: propylene), which are natural refrigerants. Unlike nonflammable R410A, however, such HC refrigerants are extremely flammable, and thus, a caution and measures are needed against refrigerant leakage.

Candidates for a low-GWP refrigerant also include an HFC refrigerant having no double bonds of carbon in its composition, such as R32 ($CH_2F_2$: difluoromethane) having a GWP lower than that of R410A.

Candidates of similar refrigerants include halogenated hydrocarbon that is a type of an HFC refrigerant similar to R32 and has double bonds of carbon in its composition. Examples of such halogenated hydrocarbon include HFO-1234yf ($CF_3CF=CH_2$: tetrafluoropropene) and HFO-1234ze ($CF_3-CH=CHF$). To distinguish from an HFC refrigerant such as R32 having no double bonds of carbon in its composition, an HFC refrigerant having double bonds of carbon is often referred to as an "HFO refrigerant" using "O" that stands for olefin (where unsaturated hydrocarbon having double bonds of carbon is called olefin).

Such a low-GWP refrigerant (such as an HFC refrigerant and an HFO refrigerant) is not as highly flammable as an HC refrigerant exemplified by R290 ($C_3H_8$: propane), which is a natural refrigerant, but unlike nonflammable R410A, has a flammability at a slightly flammable level. Thus, similarly to R290, a caution is also needed against refrigerant leakage. Refrigerant having flammability, including refrigerants at slightly flammable levels, will be hereinafter referred to as "flammable refrigerant."

In the case of using these flammable refrigerants, required standards are different from those of conventional apparatuses, and thus, a caution is needed in application. In particular, it is not desirable in terms of safety to permit an air-conditioning apparatus of an air-conditioning apparatus with a flow of a flammable refrigerant in an outdoor unit or an indoor unit provided with no fire protection units.

Thus, an air-conditioning apparatus is proposed that can stop and issue a warning when an indoor unit provided with no fire protection units is connected to the air-conditioning apparatus by comparing information on flammability of a refrigerant usable in an outdoor unit and information on flammability of a refrigerant usable in an indoor unit (see, for example, Patent Literature 1). The air-conditioning apparatus disclosed in Patent Literature 1 compares flammabilities of refrigerants usable in the outdoor unit and the indoor unit, and permits connection only when safety is assured.

CITATION LIST

Patent Literature

Patent Literature 1: Japanese Unexamined Patent Application Publication No. 2013-40730 (see, for example, Embodiment 1)

SUMMARY OF INVENTION

Technical Problem

IEC 60335-2-40, which is International Standard, defines Equation (1):

$$M = 2.5 \times (LFL)^{5/4} \times h_0 \times (A)^{1/2} \qquad (1)$$

where M is a maximum refrigerant amount [kg], A is a floor area [m²], LFL is a lower flammable limit [kg/m³] of a refrigerant, and $h_0$ is an installation height [m] of the indoor unit.

In addition, $h_0$ is defined to be 2.2 m in a ceiling type, 1.8 m in a wall type, 1.0 m in a window type, and 0.6 m in a floor type.

From Equation (1), a maximum permissible refrigerant amount based on a lower flammable limit LFL that is a physical property for each refrigerant and an installation height $h_0$ and a floor area A of an indoor unit.

On the other hand, to provide an outdoor unit in general, the number of refrigerant types that can be enclosed in the outdoor unit is limited to one type depending on refrigerating machine oil enclosed in a compressor, in terms of reliability. In providing the outdoor unit, a lower flammable limit (LFL) of a refrigerant and a maximum refrigerant amount (M) in Equation (1) are defined based on a heat exchanger volume of the outdoor unit, the presence or absence and volume of a container, and the diameter and maximum length of an extension pipe.

To determine whether an indoor unit that can be combined with an outdoor unit can be installed in an indoor space or not, it is necessary to determine the configuration, that is, an installation height $h_0$ and a floor area A, of the indoor unit. The floor area A can be obtained from Equation (2):

$$A\min = (M/(2.5 \times (LFL)^{5/4} \times h_0))^2 \qquad (2)$$

On site, the floor area A sufficient for installation needs to be obtained from $h_0$ determined based on the configuration of an indoor unit to be connected to an air-conditioning apparatus. Here, $h_0$ is obtained based on a product name on a product nameplate and the contents of an installation manual. This process is performed only on site (only by an installation operator), and $h_0$ and A might be incorrectly obtained. That is, in actual application, an operation is incorrectly performed with the indoor unit installed in an indoor space where installation is limited.

The present invention has been made to solve problems as described above, and has an object of providing an air-conditioning apparatus using a flammable refrigerant and configured to determine whether an air-conditioning operation is permitted or not by storing refrigerant amount information in an outdoor unit and installation height information in an indoor unit.

Solution to Problem

An air-conditioning apparatus according to the present invention includes at least one outdoor unit and at least one indoor unit. The air-conditioning apparatus circulates flammable refrigerant in the at least one outdoor unit and the at least one indoor unit. The at least one outdoor unit stores refrigerant amount information concerning an amount of refrigerant enclosed in the at least one outdoor unit. The at least one indoor unit stores installation height information concerning an installation height of the at least one indoor unit. The air-conditioning apparatus determines whether or not to permit an air-conditioning operation based on the refrigerant amount information and the installation height information.

Advantageous Effects of Invention

The air-conditioning apparatus according to the present invention determines whether to permit an air-conditioning operation or not based on the refrigerant amount information and the installation height information so that safety can be further ensured even in the case of using a flammable refrigerant.

BRIEF DESCRIPTION OF DRAWINGS

FIG. 3 is a table showing an example of installation height information stored in an indoor unit of the air-conditioning apparatus according to Embodiment 1 of the present invention.

FIG. 4 is a table showing an example of correspondences of determination on whether an air-conditioning operation performed by an outdoor unit of the air-conditioning apparatus according to Embodiment 1 of the present invention is permitted or not.

FIG. 5 is a table showing another example of the installation height information stored in the indoor unit of the air-conditioning apparatus according to Embodiment 1 of the present invention.

FIG. 6 is a table showing another example of the correspondences of determination on whether an air-conditioning operation performed by the outdoor unit of the air-conditioning apparatus according to Embodiment 1 of the present invention is permitted or not.

FIG. 7 is a table showing still another example of the installation height information stored in the indoor unit of the air-conditioning apparatus according to Embodiment 1 of the present invention.

FIG. 8 is a table showing still another example of the correspondences of determination on whether an air-conditioning operation performed by the outdoor unit of the air-conditioning apparatus according to Embodiment 1 of the present invention is permitted or not.

FIG. 9 is a table showing yet another example of the installation height information stored in the indoor unit of the air-conditioning apparatus according to Embodiment 1 of the present invention.

FIG. 10 is a table showing yet another example of the correspondences of determination on whether an air-conditioning operation performed by the outdoor unit of the air-conditioning apparatus according to Embodiment 1 of the present invention is permitted or not.

DESCRIPTION OF EMBODIMENTS

Figure 1:
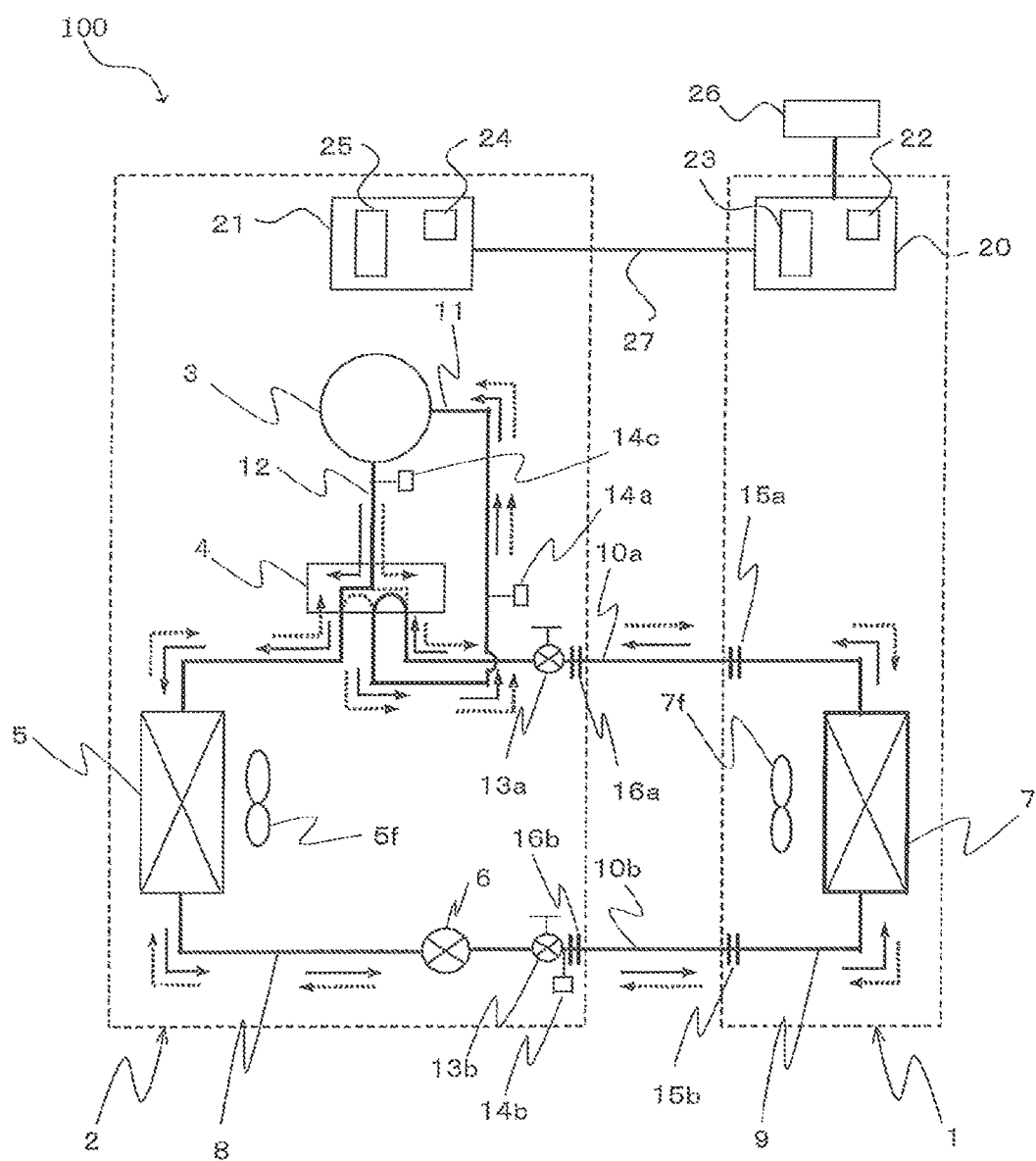
FIG. 1 schematically illustrates a refrigerant circuit configuration of an air-conditioning apparatus according to Embodiment 1 of the present invention.

Embodiments of the present invention will be described hereinafter with reference to the drawings. In the attached drawings including FIG. 1, the size relationship among components may differ from those in actual application. In the drawings, the same reference signs designate the same or components and components relevant to each other, and the same holds for the entire description of the specifications. The configurations of components in the entire specifications are merely examples, and the present invention is not limited to these examples.

Embodiment 1

FIG. 1 schematically illustrates a refrigerant circuit configuration of an air-conditioning apparatus 100 according to Embodiment 1 of the present invention. With reference to FIG. 1, a configuration and an operation of the air-conditioning apparatus 100 will be described. In Embodiment 1, the air-conditioning apparatus 100 is used as a direct expansion air-conditioning system.

As illustrated in FIG. 1, the air-conditioning apparatus 100 is a separate-type air-conditioning apparatus including an indoor unit (corresponding to a use side unit) 1 placed in, for example, a room, an outdoor unit (corresponding to a heat source side unit) 2 installed, for example, outside the room, and an extension pipe (refrigerant pipe) 10a and an extension pipe (refrigerant pipe) 10b that connect the indoor unit 1 and the outdoor unit 2 to each other. In the air-conditioning apparatus 100, a heat pump cycle is formed by causing refrigerant to circulate in the outdoor unit 2, the indoor unit 1, the extension pipe 10a, and the extension pipe 10b. The air-conditioning apparatus 100 uses a flammable refrigerant.

The outdoor unit 2 is a heat source device in the heat pump cycle, and the indoor unit 1 is a loading device (use device). That is, in general, the indoor unit 1 is placed in an air-conditioned space (including a space to which conditioned air can be supplied) and the outdoor unit 2 is installed outdoors, that is, outside the air-conditioned space.

[Configuration of Outdoor Unit 2]

(Refrigerant Circuit)

The outdoor unit 2 includes a compressor 3, a refrigerant path switching device (hereinafter referred to as a four-way valve) 4, an outdoor heat exchanger (corresponding to a heat source side heat exchanger) 5, and a pressure reducing device (hereinafter referred to as an expansion valve) 6 that are connected to each other by an outdoor refrigerant pipe (corresponding to a heat source side refrigerant pipe) 8.

The compressor 3 compresses sucked refrigerant and discharges the compressed refrigerant.

The four-way valve 4 switches a direction of a refrigerant flow in a refrigerant circuit between a cooling operation and a heating operation.

The outdoor heat exchanger 5 serves as a condenser in the cooling operation, serves as an evaporator in the heating operation, and exchanges heat between outside air and the refrigerant.

The expansion valve 6 reduces the pressure of a high-pressure refrigerant to a low pressure, and is, for example, an electronically controlled expansion valve having a changeable opening degree.

In this description, the four-way valve 4 is used as an example of a refrigerant path switching device, but a two-way valve or a three-way valve may be added in combination to constitute a refrigerant path switching device.

The cooling operation refers to an operation of supplying a low-temperature, low-pressure refrigerant to the indoor heat exchanger 7, and the heating operation refers to an operation of supplying a high-temperature, high-pressure refrigerant to the indoor heat exchanger 7.

An outdoor fan 5f for supplying (blowing) outside air to the outdoor heat exchanger 5 is disposed opposite to the outdoor heat exchanger 5. The outdoor fan 5f is rotated to generate an airflow passing through the outdoor heat exchanger 5. The outdoor unit 2 uses, for example, a propeller fan as the outdoor fan 5f, and is disposed downstream of the outdoor heat exchanger 5 (downstream of the airflow generated by the outdoor fan 5f) in such a manner that outside air is sucked through the outdoor heat exchanger 5.

(Outdoor Refrigerant Pipe)

The outdoor unit 2 includes a refrigerant pipe connecting an extension pipe connecting valve 13a at a gas-side (in the cooling operation) and the four-way valve 4, a suction pipe connected to a suction side of the compressor 3, a discharge pipe connected to a discharge side of the compressor 3, a refrigerant pipe connecting the four-way valve 4 and the outdoor heat exchanger 5, a refrigerant pipe connecting the outdoor heat exchanger 5 and the expansion valve 6, and a refrigerant pipe connecting the expansion valve 6 and an extension pipe connecting valve 13b at a liquid-side (in the cooling operation). These refrigerant pipes are collectively referred to as the outdoor refrigerant pipe 8.

For convenience of description, as illustrated in FIG. 1, a part of the outdoor refrigerant pipe 8 located at the discharge side of the compressor 3 and connecting from the compressor 3 to an inlet of the four-way valve 4 will be hereinafter referred to as a discharge pipe 12, and a part of the outdoor refrigerant pipe 8 located at the suction side of the compressor 3 and connecting from the four-way valve 4 to the compressor 3 will be hereinafter referred to as a suction pipe 11.

(Extension Pipe Connecting Valve)

The extension pipe connecting valve 13a at the gas side is disposed in a portion of the outdoor refrigerant pipe 8 connected to the gas-side extension pipe 10a. On the other hand, the extension pipe connecting valve 13b at the liquid side is disposed in a portion of the outdoor refrigerant pipe 8 connected to the liquid-side extension pipe 10b.

The extension pipe connecting valve 13a is a two-way valve that is switchable between open and closed states, and a flare joint 16a is attached to an end of the extension pipe connecting valve 13a.

The extension pipe connecting valve 13b is a three-way valve that is switchable between open and closed states, a service port 14b for use in evacuation (in preparation for supplying refrigerant to the air-conditioning apparatus 100) is attached to an end of the extension pipe connecting valve 13b, and a flare joint 16b is attached to another end of the extension pipe connecting valve 13b.

External threads are formed on portions of the flare joints 16a and 16b attached to the extension pipe connecting valves 13a and 13b (including the service port 14b) on sides facing the outdoor refrigerant pipes 8. Flare nuts (not shown) provided with internal threads are attached and engaged with the external threads in shipment (including shipment of the air-conditioning apparatus 100) of the outdoor unit 2.

(Service Port)

In any of a cooling operation or a heating operation of the air-conditioning apparatus 100, a high-temperature, high-pressure gas refrigerant compressed in the compressor 3 always flows in the discharge pipe 12, and a low-temperature, low-pressure refrigerant subjected to evaporation flows in the suction pipe 11. The low-temperature, low-pressure refrigerant flowing in the suction pipe 11 can be in a gas state in some cases or in a two-phase state in other cases.

In the air-conditioning apparatus 100, a service port 14a provided with a flare joint at a low-pressure side is connected to the suction pipe 11, and a service port 14c provided with a flare joint at the high-pressure side is connected to the discharge pipe 12. The service ports 14a and 14c are used to connect a pressure gauge in installation or test run for repair to measure an operating pressure.

External threads are formed on flare joints (not shown) of the service ports 14a and 14c, and flare nuts (not shown) are attached to the external threads in shipment (including shipment of the air-conditioning apparatus 100) of the outdoor unit 2.

(Outdoor Unit Controller)

The outdoor unit 2 includes a control board 21 serving as a controller for controlling operations of actuators such as the compressor 3, the four-way valve 4, the expansion valve 6, and the outdoor fan 5f. The control board 21 includes a memory unit 25 for storing various types of information concerning an operation of the air-conditioning apparatus 100 and a display unit 24 for displaying an abnormality in operation. The display unit 24 includes, for example, an LED, and a user or a person in charge of maintenance can determine the type of an abnormality occurring in the air-conditioning apparatus 100 based on the color and location of an illuminated LED or the number of illuminated LEDs.

The display unit 24 is preferably configured to display information concerning a flammability of a flammable refrigerant usable in the outdoor unit 2 and information concerning the amount of refrigerant enclosed in the outdoor unit 2 described later. The display unit 24 is also preferably configured to display information concerning a flammability of a flammable refrigerant usable in the indoor unit 1 and information concerning an installation height of the indoor unit 1 described later.

[Configuration of Indoor Unit 1]

(Refrigerant Circuit)

The indoor unit 1 includes an indoor heat exchanger (corresponding to a load-side heat exchanger and a use side heat exchanger) 7. The indoor heat exchanger 7 is connected to an indoor refrigerant pipe (corresponding to a use side refrigerant pipe) 9.

The indoor heat exchanger 7 serves as an evaporator in the cooling operation, serves as a condenser in the heating operation, and exchanges heat between indoor air and refrigerant.

An indoor fan 7f for supplying indoor air to the indoor heat exchanger 7 is disposed opposite to the indoor heat exchanger 7. The indoor fan 7f is rotated to generate an airflow passing through the indoor heat exchanger 7. The indoor fan 7f may be in various forms such as a cross flow fan and a turbofan appropriate to the configuration of the indoor unit 1. The indoor fan 7f is located downstream or upstream of the indoor heat exchanger 7 in the direction of the airflow generated by the indoor fan 7f.

(Connection Part to Extension Pipe)

A flare joint 15a for connecting the gas-side extension pipe 10a is disposed in a connection part of the indoor refrigerant pipe 9 connecting to the gas-side extension pipe 10a. On the other hand, a flare joint 15b for connecting the liquid-side extension pipe 10b is disposed in a connection part of the indoor refrigerant pipe 9 connecting to the liquid-side extension pipe 10b.

External threads are formed on the flare joints 15a and 15b. Flare nuts (not shown) provided with internal threads are attached and engaged with the external threads in shipment (including shipment of the air-conditioning apparatus 100) of the indoor unit 1.

(Indoor Unit Controller)

The indoor unit 1 includes a control board 20 serving as a controller for controlling the indoor fan 7f. The control board 20 includes a memory unit 23 for storing various types of information concerning an operation of the air-conditioning apparatus, and a display unit 22 including a liquid crystal screen. The display unit 22 is configured to display a set operation temperature, a room temperature, a room humidity, or an abnormality, for example. In a manner similar to the display unit 24 of the outdoor unit 2, the display unit 22 may be configured in such a manner that a user or a person in charge of maintenance can determine the type of an abnormality occurring in the air-conditioning apparatus 100 based on the color and location of an illuminated LED or the number of illuminated LEDs.

The display unit 22 is preferably configured to display information concerning a flammability of a flammable refrigerant usable in the indoor unit 1 and information concerning an installation height of the indoor unit 1 described later. The display unit 22 is also preferably configured to display information concerning a flammability of a flammable refrigerant usable in the outdoor unit 2 and information concerning the amount of refrigerant enclosed in the outdoor unit 2.

[Communication of Air-Conditioning Apparatus 100]

The control board 21 of the outdoor unit 2 and the control board 20 of the indoor unit 1 are connected to each other by an inter-unit communication line 27 to perform data communication with each other. In a room where the indoor unit 1 is installed, a remote controller 26 for communication with the control board 20 of the indoor unit 1 is provided. A user can set operation information such as a cooling operation, a heating operation, and a set temperature in the room with the remote controller 26.

The remote controller 26 preferably includes a liquid crystal screen to display a set operation temperature, a room temperature, a room humidity, or an abnormality, for example. The operation information set with the remote controller 26 is output to the control board 20 of the indoor unit 1, and is also output to the control board 21 of the outdoor unit 2 from the control board 20 through the inter-unit communication line 27. The control board 20 and the control board 21 may be connected to each other by wires or wirelessly, and the control board 20 and the remote controller 26 may also be connected to each other by wires or wirelessly.

[Refrigerant Circuit of Air-Conditioning Apparatus 100]

The gas-side extension pipe 10a has one end detachably connected to the flare joint 16a attached to the gas-side extension pipe connecting valve 13a of the outdoor unit 2 and the other end detachably connected to the flare joint 15a attached to the indoor refrigerant pipe 9 of the indoor unit 1.

On the other hand, the liquid-side extension pipe 10b has one end detachably connected to the flare joint 16b attached to the liquid-side extension pipe connecting valve 13b of the outdoor unit 2 and the other end detachably connected to the flare joint 15b attached to the indoor refrigerant pipe 9 of the indoor unit 1.

That is, the outdoor refrigerant pipe 8 and the indoor refrigerant pipe 9 are connected to each other by the extension pipes 10a and 10b to form a refrigerant circuit, and a compression heat pump cycle in which refrigerant compressed in the compressor 3 circulates is formed.

[Normal Operation of Air-Conditioning Apparatus 100]

(Refrigerant Flow in Cooling Operation)

In FIG. 1, solid arrows represent a direction of a refrigerant flow in a cooling operation of the air-conditioning apparatus 100. In the cooling operation, the four-way valve 4 is switched to a state indicated by the solid arrows so that a low-temperature, low-pressure refrigerant is supplied to the indoor heat exchanger 7 in the refrigerant circuit.

A high-temperature, high-pressure gas refrigerant discharged from the compressor 3 first flows into the outdoor heat exchanger 5 through the four-way valve 4. In the cooling operation, the outdoor heat exchanger 5 serves as a condenser. That is, while the airflow generated by rotation of the outdoor fan 5f is passing through the outdoor heat exchanger 5, the outdoor air passing through the outdoor heat exchanger 5 and refrigerant flowing in the outdoor heat exchanger 5 exchange heat so that heat of condensation of the refrigerant is given to the outdoor air. In this manner, the refrigerant is condensed in the outdoor heat exchanger 5 and turns into high-pressure, intermediate-temperature liquid refrigerant. Next, the high-pressure, intermediate-temperature liquid refrigerant flows into the expansion valve 6, adiabatically expands in the expansion valve 6 to turn into low-pressure, low-temperature two-phase refrigerant.

Thereafter, the low-pressure, low-temperature two-phase refrigerant is supplied to the indoor unit 1 via the liquid-side extension pipe 10b and flows into the indoor heat exchanger 7. In the cooling operation, the indoor heat exchanger 7 serves as an evaporator. That is, while a flow of indoor air generated by rotation of the indoor fan 7f is passing through the indoor heat exchanger 7, the indoor air passing through the indoor heat exchanger 7 and refrigerant flowing in the indoor heat exchanger 7 exchange heat so that the refrigerant takes heat of vaporization (heating energy) from the indoor air and evaporates to turn into low-temperature, low-pressure gas refrigerant or refrigerant in a two-phase state. On the other hand, the indoor air passing through the indoor heat exchanger 7 takes cooling energy from the refrigerant to be cooled, thereby cooling an air-conditioned space (such as a room).

Further, the low-temperature, low-pressure gas refrigerant or the refrigerant in the two-phase state that has evaporated in the indoor heat exchanger 7 is supplied to the outdoor unit 2 via the gas-side extension pipe 10a, and is sucked into the compressor 3 via the four-way valve 4. This refrigerant is compressed in the compressor 3 to turn into high-temperature, high-pressure gas refrigerant again. This cycle is repeated in the cooling operation.

(Refrigerant Flow in Heating Operation)

In FIG. 1, dotted arrows represent a direction of a refrigerant flow in a heating operation of the air-conditioning apparatus 100. In the heating operation, the four-way valve 4 is switched to a state indicated by the dotted arrows so that a high-temperature, high-pressure refrigerant is supplied to the indoor heat exchanger 7 in the refrigerant circuit. Specifically, refrigerant flows in a direction opposite to the direction in the cooling operation, and first flows into the indoor heat exchanger 7. The indoor heat exchanger 7 serves as a condenser and the outdoor heat exchanger 5 serves as an evaporator so that heat of condensation (heating energy) is given to indoor air passing through the indoor heat exchanger 7. In this manner, a heating operation is performed.

[Refrigerant Used in Air-Conditioning Apparatus 100]

In the air-conditioning apparatus 100, refrigerant flowing in the refrigerant circuit is R32 ($CH_2F_2$; difluoromethane), which is a slightly flammable HFC refrigerant, having a GWP smaller than that of R410A currently widely used in air-conditioning apparatuses, and having a relatively small influence on global warming. In general, a certain amount of refrigerant is enclosed in the outdoor unit 2 before shipment. In installation, when the amount of refrigerant is found insufficient because of the lengths of extension pipes that differ from one another depending on situations of installation sites, refrigerant is additionally supplied in an on-site job as an installation manual instructs. The refrigerant amount in a case where the length of the extension pipes is at maximum is a maximum refrigerant amount.

The refrigerant used in the air-conditioning apparatus 100 is not limited to R32, and may be the above-described HFO refrigerant that is slightly flammable similarly to R32, is of a type of an HFC refrigerant, but is halogenated hydrocarbon having double bonds of carbon in its composition, and is, for example, HFO-1234yf ($CF_3CF=CH_2$: tetrafluoropropene) or HFO-1234ze ($CF_3—CH=CHF$) having a GWP smaller than that of R32 refrigerant.

The refrigerant may be a highly flammable HC refrigerant such as R290 ($C_3H_8$: propane) and R1270 ($C_3H_6$: propylene).

The refrigerant may be a mixed refrigerant as a mixture of two or more types of these refrigerants.

If such a refrigerant leaks from the indoor unit 1, a concentration of refrigerant may reach a flammable concentration range depending on the amount of leaked refrigerant. Because these refrigerants have densities higher than the air under an atmospheric pressure, even with the same amount of leaked refrigerant, the concentration of refrigerant reaches the flammable concentration range in some cases and does not reach the flammable concentration range in other cases, depending on the installation height of the indoor unit 1, that is, depending on whether the indoor unit 1 is a ceiling type, a wall type, a window type, or a flow type.

For this reason, in the air-conditioning apparatus 100, it is determined whether an air-conditioning operation (such as a cooling operation and a heating operation) is permitted or not by referring to the maximum refrigerant amount of the outdoor unit 2 and the installation height of the indoor unit 1. Thus, the air-conditioning apparatus 100 is configured to secure further safety. The details will be described below.

[Control Process of Air-Conditioning Apparatus 100]

Figure 2:
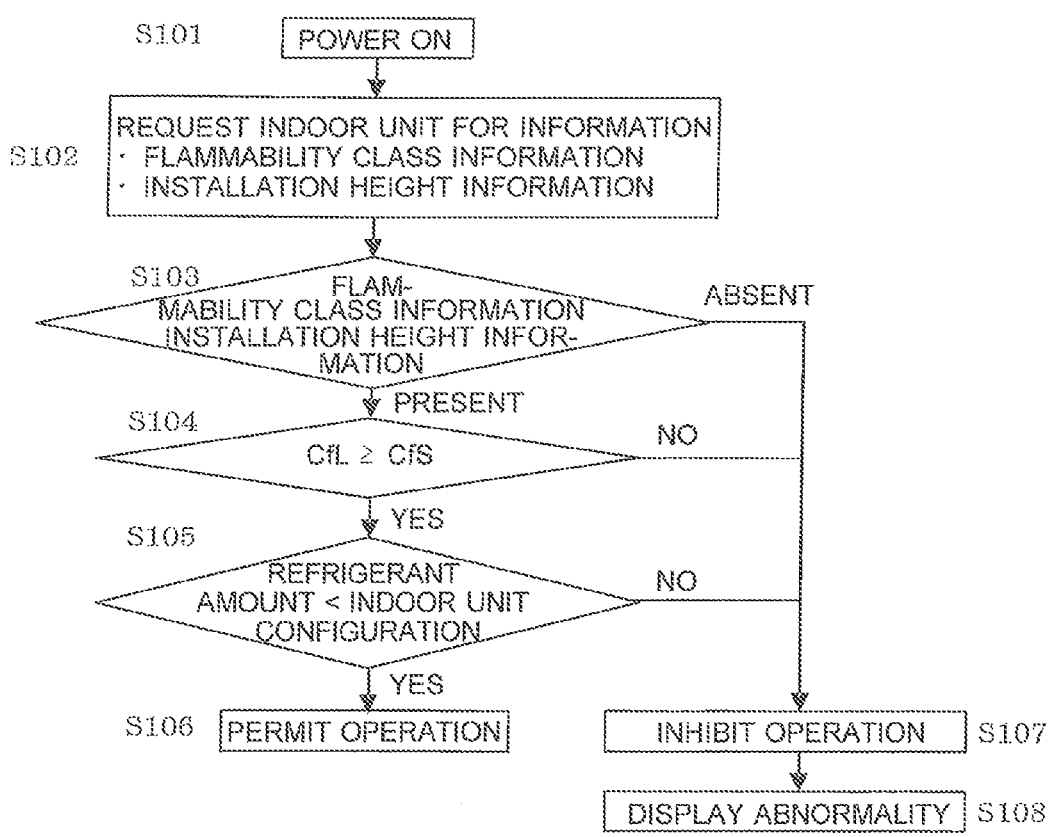
FIG. 2 is a flowchart illustrating a flow in a control process of the air-conditioning apparatus according to Embodiment 1 of the present invention.

FIG. 2 is a flowchart illustrating a flow in a control process of the air-conditioning apparatus 100. FIG. 3 is a table showing an example of installation height information stored in the indoor unit 1 of the air-conditioning apparatus 100. FIG. 4 is a table showing an example of correspondences of determination on whether an air-conditioning operation performed by the outdoor unit 2 of the air-conditioning apparatus 100 is permitted or not. With reference to FIGS. 2 to 4, a flow in control process of the air-conditioning apparatus 100 will be described. Detailed description on a flammability class CfS and a flammability class CfL is based on Japanese Unexamined Patent Application Publication No. 2012-159216.

The memory unit 25 provided in the control board 21 of the outdoor unit 2 stores a flammability class CfS (first information) that is information on flammability of a flammable refrigerant usable in the outdoor unit 2. The memory unit 25 provided in the control board 21 of the outdoor unit 2 stores refrigerant amount information that is the maximum refrigerant amount that can be enclosed in the outdoor unit 2. In general, the maximum length of installable extension pipes is defined in the outdoor unit 2, and consequently, the maximum refrigerant amount is previously defined. The flammability class CfS stored in the memory unit 25 is preferably changeable.

The memory unit 23 provided in the control board 20 of the indoor unit 1 stores a flammability class CfL (second information) that is information on flammability of a flammable refrigerant usable in the indoor unit 1.

The memory unit 23 provided in the control board 20 of the indoor unit 1 stores information on the installation height of the indoor unit 1 as installation height information. The installation height information is stored in a state in which the information is specified for each installation height of the indoor unit 1, as shown in FIG. 3, for example. The example shown in FIG. 3 is based on the contents defined in International Standard IEC 60335-2-40. International Standard can be changed in some cases, and thus, the installation height information and the flammability class CfL stored in the memory unit 23 are preferably changeable.

In the air-conditioning apparatus 100, the outdoor unit 2 and the indoor unit 1 are connected to each other by the extension pipe 10a, the extension pipe 10b, and the inter-unit communication line 27. In this state, when electric power is supplied to the air-conditioning apparatus 100, communication automatically starts between the control board 21 of the outdoor unit 2 and the control board 20 of the indoor unit 1 (step S101). Once the communication starts, the control board 21 of the outdoor unit 2 instructs the control board 20 of the indoor unit 1 to notify the control board 21 of the corresponding flammability class CfL and installation height information (step S102).

The instructed control board 20 of the indoor unit 1 notifies the control board 21 of the outdoor unit 2 of whether the flammability class CfL and the installation height information stored in the memory unit 23 are present or not (step S103). When the flammability class CfL and the installation height information are not present, that is, do not return (step S103, ABSENT), the control board 21 of the outdoor unit 2 inhibits operations of devices (step S107), and displays an abnormality on at least one of the outdoor unit 2, the indoor unit 1, and the remote controller 26 (step S108).

When the flammability class CfL and the installation height information are present (step S103, PRESENT), the notified control board 21 of the outdoor unit 2 compares the flammability class CfS stored in the memory unit 25 and the flammability class CfL (step S104). When a relationship of CfL<CfS is satisfied (step S104, NO), the control board 21 of the outdoor unit 2 determines that a flammable refrigerant usable in the outdoor unit 2 is more flammable than a flammable refrigerant usable in the indoor unit 1, inhibits operations of devices in the indoor unit 1 (step S107), and displays an abnormality on at least one of the outdoor unit 2, the indoor unit 1, and the remote controller 26 (step S108).

When a relationship of CfL≥CfS is satisfied (step S104, YES), the control board 21 of the outdoor unit 2 determines that the flammable refrigerant usable in the outdoor unit 2 is less flammable than the flammable refrigerant usable in the indoor unit 1, and refers to the refrigerant amount information stored in the memory unit 25 of the outdoor unit 2 and the installation height information of the indoor unit 1 (step S105). Specifically, as shown in FIG. 4, the control board 21 of the outdoor unit 2 refers to refrigerant amount information previously set such as "LARGEST," "LARGE," "MEDIUM," and "SMALL" and the installation height information of the indoor unit 1 set for each installation height of the indoor unit 1, and determines whether an air-conditioning operation is permitted or not. That is, the control board 21 of the outdoor unit 2 determines whether the installation height of the indoor unit 1 can assure safety even when the amount of refrigerant enclosed in the outdoor unit 2 is within a permissible range.

Even with the same amount of leaked refrigerant, the concentration of refrigerant reaches the flammable concentration range in the installation space of the indoor unit 1 in some cases and does not reach the flammable concentration range in other cases, depending on the difference in installation height of the indoor unit 1. Whether a concentration of refrigerant reaches the flammable concentration range or not is previously examined and is set depending on the installation height of the indoor unit 1 so that a guide for the installation height of the indoor unit 1 that assures safety can be determined for the maximum amount of refrigerant enclosed in the outdoor unit 2. Thus, the air-conditioning apparatus 100 determines whether an air-conditioning operation is permitted or not by referring to the refrigerant amount information of the outdoor unit 2 and the installation height information of the indoor unit 1. Equation (1) defined by International Standard is a standard for determining whether the concentration of refrigerant reaches the flammable concentration range depending on the difference in installation height of the indoor unit 1. That is, the air-conditioning apparatus 100 automatically obtains information on the amount of enclosed refrigerant defined by International Standard, and determines whether to permit an air-conditioning operation or not based on the refrigerant amount information stored in the outdoor unit 2 and the installation height information stored in the indoor unit 1. In the process of obtaining the information on the refrigerant amount, a floor area is only required to be stored in the outdoor unit 2 as minimum floor area information defined in, for example, specifications or a catalog.

For example, when the refrigerant amount information is "LARGEST," and the indoor unit 1 is determined to be of a ceiling type, the control board 21 of the outdoor unit 2 permits an air-conditioning operation. In other words, in this case, when the indoor unit 1 is of a wall type, a window type, or a floor type, the air-conditioning operation is not permitted.

When the refrigerant amount information is "LARGE," and the indoor unit 1 is determined to be of a ceiling type or a wall type, the control board 21 of the outdoor unit 2 permits an air-conditioning operation. In other words, in this case, when the indoor unit 1 is of a window type or a floor type, the air-conditioning operation is not permitted.

When the refrigerant amount information is determined to be "MEDIUM," and the indoor unit 1 is determined to be of a ceiling type, a wall type, or a window type, the control board 21 of the outdoor unit 2 permits an air-conditioning operation. In other words, in this case, when the indoor unit 1 is of a floor type, the air-conditioning operation is not permitted.

When the refrigerant amount information is "SMALL," the control board 21 of the outdoor unit 2 permits an air-conditioning operation, independently of the installation height of the indoor unit 1.

When it is determined that the installation height is not satisfied (step S105, NO), the control board 21 of the outdoor unit 2 inhibits operations of devices (step S107), and displays an abnormality on at least one of the outdoor unit 2, the indoor unit 1, and the remote controller 26 (step S108).

On the other hand, when it is determined that the installation height is satisfied (step S105, YES), the control board 21 of the outdoor unit 2 permits an air-conditioning operation (step S106), and does not display an abnormality.

When an air-conditioning operation is to be inhibited, it is desirable to inhibit an operation in an initial state of the air-conditioning apparatus 100.

As described above, when connection cannot be permitted based on the installation height information of the indoor unit 1, the air-conditioning apparatus 100 inhibits an air-conditioning operation. Thus, the air-conditioning apparatus 100 can determine whether to permit an air-conditioning operation in consideration of installation height information of the indoor unit 1, thereby assuring safety. When the air-conditioning apparatus 100 can ensure safety, devices can be flexibly combined. In addition, the air-conditioning apparatus 100 can minimize a change in specifications along with a change of refrigerants to be used, and thus, reduction in costs for development of the apparatus, shortening of delivery times, and savings of resources and energy can be achieved. In addition, when a new outdoor unit using a different refrigerant is to be installed to an existing system, for example, the air-conditioning apparatus 100 can use an existing indoor unit and does not need to update the indoor unit concurrently with the installation of the new outdoor unit, thus contributing to savings of resources and energy and shortening of a work period.

Furthermore, when the corresponding flammability class of the indoor unit 1 is lower than the corresponding flammability class of the outdoor unit 2, an air-conditioning operation is inhibited. Even when the corresponding flammability class of the indoor unit 1 is greater than or equal to the corresponding flammability class of the outdoor unit 2, and connection cannot be permitted based on the installation height information of the indoor unit, an air-conditioning operation is inhibited. Thus, even if the indoor unit is erroneously connected, safety can be assured. When the air-conditioning operation is to be inhibited, an abnormality is displayed. Thus, an operator can take measures promptly.

In Embodiment 1, the indoor unit 1 is instructed by the outdoor unit 2 to notify the outdoor unit 2 of a flammability class and refrigerant amount information of the outdoor unit.

Alternatively, the indoor unit 1 may instruct the outdoor unit 2, and the remote controller 26 may instruct the outdoor unit 2 and the indoor unit 1 so that the remote controller 26 can determine permission or inhibition of an air-conditioning operation. The flammability class and refrigerant amount information of the outdoor unit and installation height information of the indoor unit are stored in the memories. Alternatively, a switch or a jumper wire for setting a flammability class, refrigerant amount information of the outdoor unit, and installation height information of the indoor unit may be provided so that these types of information are previously set in fabrication of the apparatus.

<Variation 1>

FIG. 5 is a table showing another example of the installation height information stored in the indoor unit 1 of the air-conditioning apparatus 100. FIG. 6 is a table showing another example of the correspondences on determination on whether an air-conditioning operation performed by the outdoor unit 2 of the air-conditioning apparatus 100 is permitted or not. With reference to FIGS. 5 and 6, Variation 1 of determination on whether an air-conditioning operation of the air-conditioning apparatus 100 is permitted or not will be described.

FIG. 3 shows an example in which the installation height information of the indoor unit 1 is stored in a state in which the information is specified for each installation height of the indoor unit 1. That is, based on the contents defined by International Standard, IEC 60335-2-40, the installation height information of the indoor unit 1 is specified in such a manner that information 1 is for a ceiling type, information 2 is for a wall type, information 3 is for a window type, and information 4 is for a floor type.

In the example shown in FIG. 4, the refrigerant amount information is set in four stages ("LARGEST," "LARGE," "MEDIUM," and "SMALL") that are each referred to corresponding part of the installation height information of the indoor unit 1 to determine whether an air-conditioning operation is permitted or not.

On the other hand, in the example shown in FIG. 5, the installation height information of the indoor unit 1 is stored in a state in which the installation height of the indoor unit 1 is divided into two groups and each of these groups is specified. That is, the installation height information of the indoor unit 1 is specified in such a manner that the information 1 is for a ceiling type or a wall type, and information 2 is for a window type or a floor type.

In FIG. 6, the refrigerant amount information is divided into two stages ("LARGE" and "SMALL"). Each of the stages is referred to corresponding part of the installation height information (information 1 and information 2) of the indoor unit 1 based on the table of FIG. 5 to determine whether an air-conditioning operation is permitted or not.

For example, when the refrigerant amount information is "LARGE," and the indoor unit 1 is determined to be of a ceiling type or a wall type, the control board 21 of the outdoor unit 2 permits an air-conditioning operation. In other words, in this case, when the indoor unit 1 is of a window type or a floor type, the air-conditioning operation is not permitted.

When the refrigerant amount information is "SMALL," the control board 21 of the outdoor unit 2 permits an air-conditioning operation, independently of the installation height of the indoor unit 1.

<Variation 2>

FIG. 7 is a table showing still another example of the installation height information stored in the indoor unit 1 of the air-conditioning apparatus 100. FIG. 8 is a table showing still another example of the correspondences of determination on whether an air-conditioning operation performed by the outdoor unit 2 of the air-conditioning apparatus 100 is permitted or not. With reference to FIGS. 7 and 8, Variation 2 of determination on whether an air-conditioning operation of the air-conditioning apparatus 100 is permitted or not will be described.

FIG. 7 shows an example in which the installation height information of the indoor unit 1 is stored in a state in which the installation height of the indoor unit 1 is divided into three groups. That is, the installation height information of the indoor unit 1 is specified in such a manner that information 1 is for a ceiling type or a wall type, information 2 is for a window type, and information 3 is for a floor type.

In FIG. 8, the refrigerant amount information is set in three stages ("LARGEST", "LARGE," and "SMALL"). Each of the stages is referred to corresponding part of the installation height information (information 1 to 3) of the indoor unit 1 based on the table shown in FIG. 7 to determine whether an air-conditioning operation is permitted or not.

For example, when the refrigerant amount information is "LARGEST," and the indoor unit 1 is determined to be of a ceiling type or a wall type, the control board 21 of the outdoor unit 2 permits an air-conditioning operation. In other words, in this case, when the indoor unit 1 is of a window type or a floor type, the air-conditioning operation is not permitted.

When the refrigerant amount information is "LARGE," and the indoor unit 1 is determined to be of a ceiling type, a wall type, or a window type, the control board 21 of the outdoor unit 2 permits an air-conditioning operation. In other worlds, in this case, when the indoor unit 1 is of a floor type, an air-conditioning operation is not permitted.

When the refrigerant amount information is "SMALL," the control board 21 of the outdoor unit 2 permits an air-conditioning operation, independently of the installation height of the indoor unit 1.

<Variation 3>

FIG. 9 is a table showing yet another example of the installation height information stored in the indoor unit 1 of the air-conditioning apparatus 100. FIG. 10 is a table showing yet another example of the correspondences of determination on whether an air-conditioning operation performed by the outdoor unit 2 of the air-conditioning apparatus 100 is permitted or not. With reference to FIGS. 9 and 10, Variation 3 of determination on whether an air-conditioning operation of the air-conditioning apparatus 100 is permitted or not will be described.

FIG. 9 shows an example in which the installation height information of the indoor unit 1 is stored in a state in which the installation height of the indoor unit 1 is divided into three groups. That is, the installation height information of the indoor unit 1 is specified in such a manner that information 1 is for a ceiling type, information 2 is for a wall type, and information 3 is for a window type or a floor type. In FIG. 9, the contents of the information 1 and the information 3 are different from those of the information 1 and the information 3 shown in FIG. 7.

In FIG. 10, the refrigerant amount information is set in three stages ("LARGEST", "LARGE," and "SMALL"). Each of the stages is referred to corresponding part of the installation height information (information 1 to 3) of the indoor unit 1 based on the table shown in FIG. 9 to determine whether an air-conditioning operation is permitted or not.

For example, when the refrigerant amount information is "LARGEST," and the indoor unit 1 is determined to be of a ceiling type, the control board 21 of the outdoor unit 2 permits an air-conditioning operation. In other words, in this case, when the indoor unit 1 is of a wall type, a window type, or a floor type, the air-conditioning operation is not permitted.

When the refrigerant amount information is "LARGE," and the indoor unit 1 is determined to be of a ceiling type or a wall type, the control board 21 of the outdoor unit 2 permits an air-conditioning operation. In other worlds, in this case, when the indoor unit 1 is of a window type or a floor type, an air-conditioning operation is not permitted.

When the refrigerant amount information is "SMALL," the control board 21 of the outdoor unit 2 permits an air-conditioning operation, independently of the installation height of the indoor unit 1.

As described above, the installation height information stored in the indoor unit 1 of the air-conditioning apparatus 100 can be set appropriately to the installation height of the indoor unit 1. Thus, the air-conditioning apparatus 100 can determine whether to permit an air-conditioning operation depending on installation height of the indoor unit 1, thereby further assuring safety. As described above, the installation height information stored in the indoor unit 1 is preferably changeable.

Embodiment 2

Figure 11:
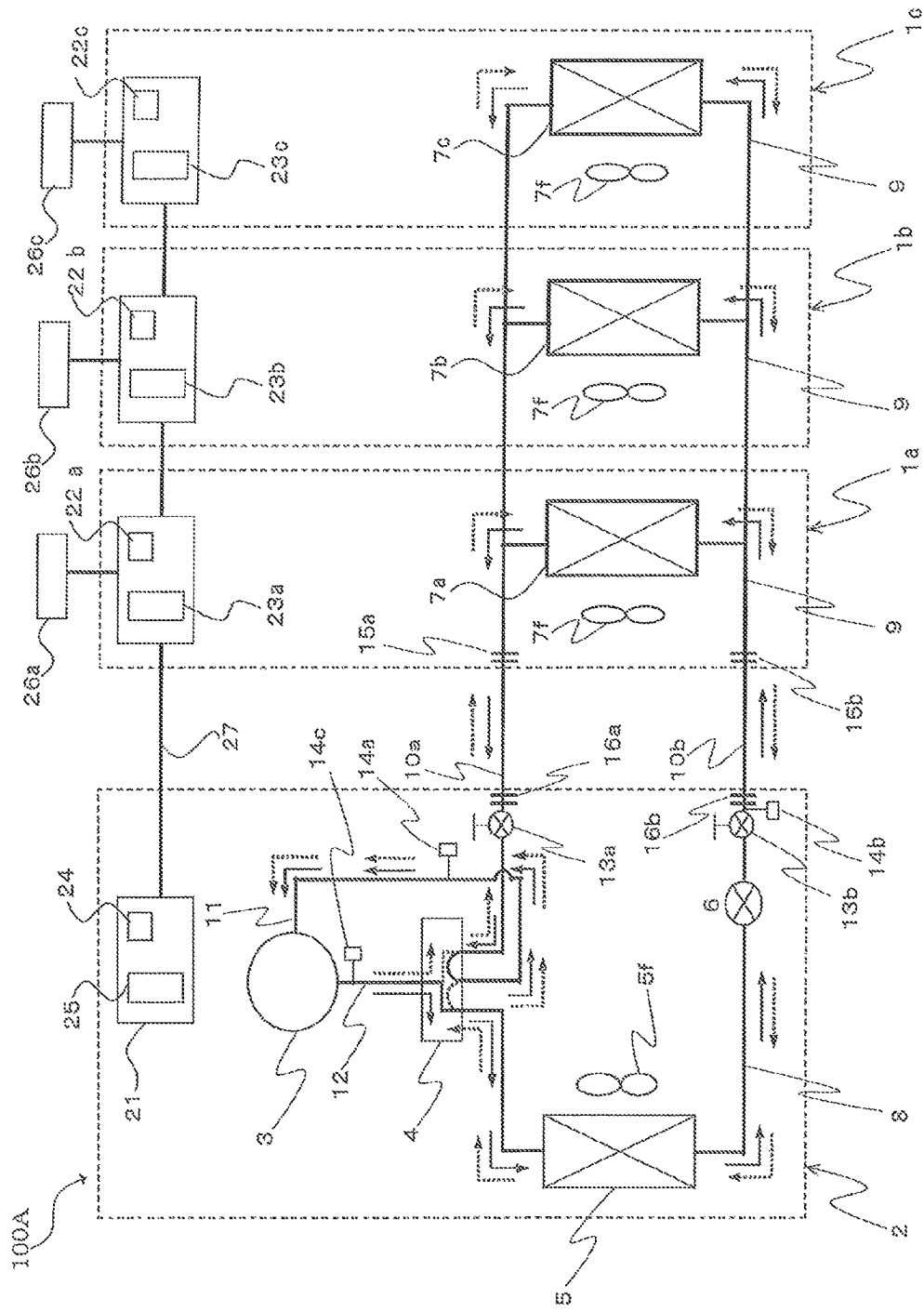
FIG. 11 schematically illustrates a refrigerant circuit configuration of an air-conditioning apparatus according to Embodiment 2 of the present invention.

FIG. 11 schematically illustrates a refrigerant circuit configuration of an air-conditioning apparatus 100A according to Embodiment 2 of the present invention. With reference to FIG. 11, a configuration and an operation of the air-conditioning apparatus 100A will be described. In Embodiment 2, in a manner similar to the description of the air-conditioning apparatus 100 according to Embodiment 1, the air-conditioning apparatus 100A used as a direct expansion air-conditioning system will be described. In Embodiment 2, the same reference signs designate the same parts in Embodiment 1, and aspects different from those of Embodiment 1 will be mainly described.

Embodiment 1 is directed to the air-conditioning apparatus 100 in which one indoor unit 1 is connected to one outdoor unit 2. On the other hand, Embodiment 2 is directed to the air-conditioning apparatus 100A in which a plurality of indoor units 1 (indoor units 1a to 1c) are connected to one outdoor unit 2.

As illustrated in FIG. 11, in the air-conditioning apparatus 100A, three indoor units 1 are connected to one outdoor unit 2. The indoor unit 1a, the indoor unit 1b, and the indoor unit 1c are connected in parallel to a liquid pipe (an extension pipe 10b) and a gas pipe (an extension pipe 10a). Indoor heat exchangers 7a to 7c are the same as the indoor heat exchanger 7 of Embodiment 1.

The indoor unit 1a, the indoor unit 1b, and the indoor unit 1c include a control board 20a, a control board 20b, and a control board 20c, respectively, that are connected to a control board 21 via an inter-unit communication line 27. The control board 20a, the control board 20b, and the control board 20c are connected to a remote controller 26a, a remote controller 26b, and a remote controller 26c, respectively. A user operates the remote controller 26a, the remote controller 26b, and the remote controller 26c to set operation information of the indoor unit 1a, the indoor unit 1b, and the indoor unit 1c. The control boards 20a to 20c are the same as the control board 20 of Embodiment 1. The remote controllers 26a to 26c are the same as the remote controller 26 of Embodiment 1.

In Embodiment 1, the flammability class CfS of the outdoor unit 2 and the flammability class CfL of the indoor unit 1 are compared, and the refrigerant amount information of the outdoor unit 2 and the installation height information of the indoor unit 1 are referred. In Embodiment 2, the multiple indoor units 1 are provided, and thus a flammability class CfS of the outdoor unit 2 is compared with flammability classes CfL of the indoor units 1.

In the air-conditioning apparatus 100A, the outdoor unit 2 is connected to the indoor units 1 by the extension pipe 10a, the extension pipe 10b, and the inter-unit communication line 27. In this state, when electric power is supplied to the air-conditioning apparatus 100A, communication automatically starts between the control board 21 of the outdoor unit 2 and the control boards 20 of the indoor units 1. Once the communication starts, the control board 21 of the outdoor unit 2 instructs the control boards 20 of the indoor units 1 to notify the control board 21 of the corresponding flammability classes CfL and installation height information.

The instructed control boards 20 of the indoor units 1 notify the control board 21 of the outdoor unit 2 of whether flammability classes CfL and installation height information are stored in the memory units 23 (memory units 23a to 23c) or not. When at least one of the instructed indoor units 1 does not store the flammability class CfL and the installation height information, that is, the flammability class CfL and the installation height information do not return, the control board 21 of the outdoor unit 2 inhibits operations of devices, and displays an abnormality on at least one of the outdoor unit 2, the indoor units 1, and the remote controllers 26.

When the flammability class CfL and the installation height information are present, the notified control board 21 of the outdoor unit 2 compares a flammability class CfS stored in the memory unit 25 and the flammability classes CfL. When at least one of the flammability classes CfL satisfies the relationship of CfL<CfS, the control board 21 of the outdoor unit 2 inhibits operations of devices, and displays an abnormality on at least one of the outdoor unit 2, the indoor units 1, and the remote controllers 26.

When all the flammability classes CfL satisfies the relationship of CfL≥CfS, the control board 21 of the outdoor unit 2 refers to the refrigerant amount information stored in the memory unit 25 of the outdoor unit 2 and the installation height information of the indoor units 1. When it is determined that the installation heights of all the indoor units 1 are not satisfied, the control board 21 of the outdoor unit 2 inhibits operations of devices, and displays an abnormality on at least one of the outdoor unit 2, the indoor units 1, and the remote controllers 26. On the other hand, when it is determined that the installation heights of all the indoor units 1 are satisfied, the control board 21 of the outdoor unit 2 permits an air-conditioning operation and does not display an abnormality.

When an air-conditioning operation is to be inhibited, it is desirable to inhibit an operation in an initial state of the air-conditioning apparatus 100A.

Embodiment 3

Figure 12:
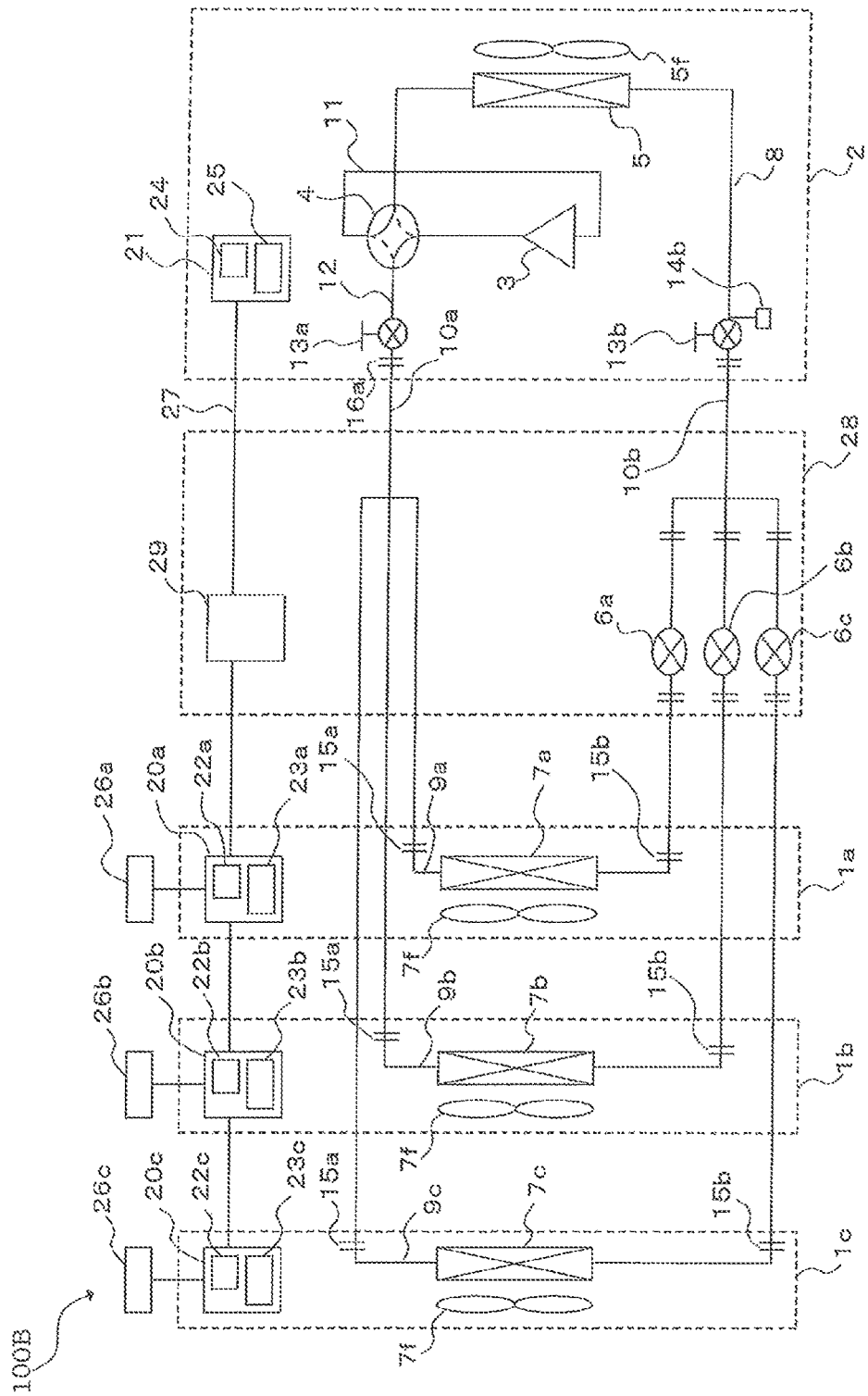
FIG. 12 schematically illustrates a refrigerant circuit configuration of an air-conditioning apparatus according to Embodiment 3 of the present invention.

FIG. 12 schematically illustrates a refrigerant circuit configuration of an air-conditioning apparatus 100B according to Embodiment 3 of the present invention. With reference to FIG. 12, a configuration and an operation of the air-conditioning apparatus 100B will be described. In Embodiment 3, in a manner similar to the description of the air-conditioning apparatus 100 according to Embodiment 1, the air-conditioning apparatus 100B used as a direct expansion air-conditioning system will be described. In Embodiment 3, the same reference signs designate the same parts in Embodiments 1 and 2, and aspects different from those of Embodiments 1 and 2 will be mainly described.

Embodiment 1 is directed to the air-conditioning apparatus 100 in which one indoor unit 1 is connected to one outdoor unit 2. On the other hand, Embodiment 3 is directed to the air-conditioning apparatus 100B in which a plurality of indoor units 1 (indoor units 1a to 1c) are connected to one outdoor unit 2, as in Embodiment 2. In Embodiment 3, however, a branch box 28 for dividing refrigerant is interposed between the outdoor unit 2 and the indoor units 1a to 1c so that refrigerant from the outdoor unit 2 is divided at the branch box 28 and is supplied to the indoor units 1a to 1c. The air-conditioning apparatus 100B is configured so that the indoor units 1 can operate independently of each other.

In the branch box 28, an extension pipe 10a and an extension pipe 10b branch depending on the number of indoor units 1 connected to the branch box 28. Expansion valves 6 (expansion valves 6a to 6c) are individually provided in the branched extension pipes 10b. The branch box 28 includes a branch box control board 29. The branch box control board 29 is connected between the control board 21 of the outdoor unit 2 and control boards 20 (control boards 20a to 20c) of the indoor unit 1 to relay communication.

In the air-conditioning apparatus 100B, the outdoor unit 2, the indoor units 1, and the branch box 28 are connected to each other by the extension pipe 10a, the extension pipe 10b, and the inter-unit communication line 27. In this state, when electric power is supplied to the air-conditioning apparatus 100B, communication automatically starts between the control board 21 of the outdoor unit 2 and the control boards 20 of the indoor units 1 through the branch box control board 29. Once the communication starts, the control board 21 of the outdoor unit 2 instructs the control boards 20 of the indoor units 1 to notify the control board 21 of the corresponding flammability classes CfL and installation height information.

The instructed control boards 20 of the indoor units 1 notify the control board 21 of the outdoor unit 2 of whether flammability classes CfL and installation height information are stored in the memory units 23 (memory units 23a to 23c) or not. When at least one of the instructed indoor units 1 does not store the flammability class CfL and the installation height information, that is, the flammability class CfL and the installation height information do not return, the control board 21 of the outdoor unit 2 inhibits operations of devices in the indoor unit 1 whose flammability class CfL and installation height information do not return, and displays an abnormality on at least one of the outdoor unit 2, the indoor units 1, and the remote controllers 26. In addition, the expansion valves 6 in the branch box 28 are fully closed so that refrigerant does not flow.

When the flammability classes CfL and the installation height information are stored, the notified control board 21 of the outdoor unit 2 compares a flammability class CfS stored in the memory unit 25 and the flammability classes CfL. When at least one of the flammability classes CfL satisfies the relationship of CfL<CfS, the control board 21 of the outdoor unit 2 inhibits operations of devices in the indoor unit 1 having this flammability class CfL, and displays an abnormality on at least one of the outdoor unit 2, the indoor unit 1, and the remote controllers 26.

When all the flammability classes CfL satisfy the relationship of CfL≥CfS, the control board 21 of the outdoor unit 2 refers to the refrigerant amount information stored in the memory unit 25 of the outdoor unit 2 and the installation height information of the indoor units 1. When it is determined that the installation height of at least one of the indoor units 1 is not satisfied, the control board 21 of the outdoor unit 2 inhibits operations of devices in this indoor unit 1, and displays an abnormality on at least one of the outdoor unit 2, the indoor unit 1 whose installation height is not satisfied, and the corresponding remote controller 26. In addition, the expansion valves 6 in the branch box 28 to which the indoor unit 1 whose installation height is not satisfied is connected is fully closed so that refrigerant does not flow.

On the other hand, the control board 21 of the outdoor unit 2 permits an air-conditioning operation of the indoor unit 1 whose installation height is satisfied, and does not display an abnormality.

When an air-conditioning operation is to be inhibited, it is desirable to inhibit an operation in an initial state of the air-conditioning apparatus 100B.

Embodiment 4

Figure 13:
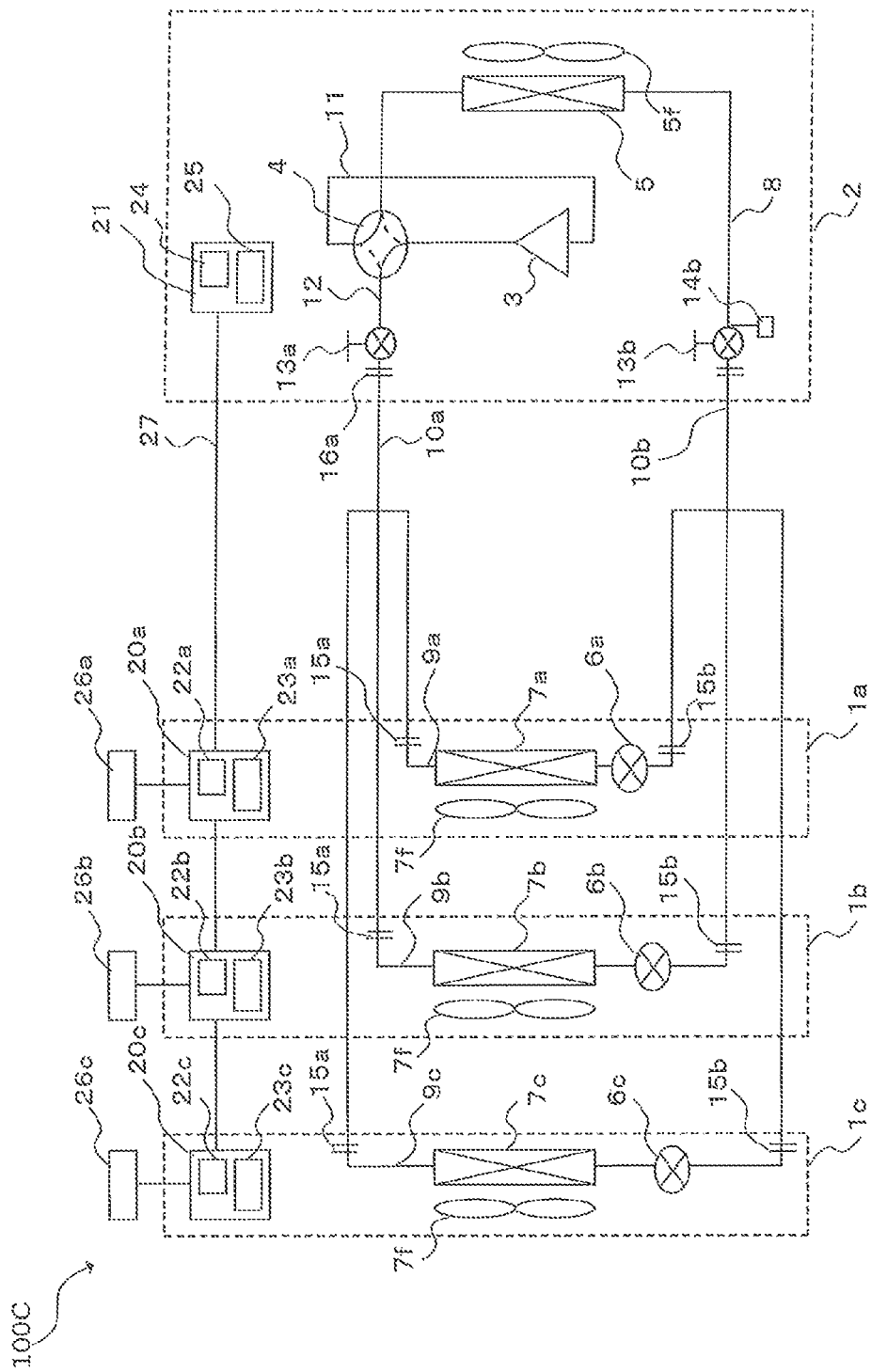
FIG. 13 schematically illustrates a refrigerant circuit configuration of an air-conditioning apparatus according to Embodiment 4 of the present invention.

FIG. 13 schematically illustrates a refrigerant circuit configuration of an air-conditioning apparatus 100C according to Embodiment 4 of the present invention. With reference to FIG. 13, a configuration and an operation of the air-conditioning apparatus 100C will be described. In Embodiment 4, in a manner similar to the description of the air-conditioning apparatus 100 according to Embodiment 1, the air-conditioning apparatus 100C used as a direct expansion air-conditioning system will be described. In Embodiment 4, the same reference signs designate the same parts in Embodiments 1 to 3, and aspects different from those of Embodiments 1 to 3 will be mainly described.

Embodiment 1 is directed to the air-conditioning apparatus 100 in which one indoor unit 1 is connected to one outdoor unit 2. On the other hand, Embodiment 4 is directed to the air-conditioning apparatus 100C in which a plurality of indoor units 1 (indoor units 1a to 1c) are connected to one outdoor unit 2, as in Embodiment 3. The air-conditioning apparatus 100C is configured so that the indoor units 1 can operate independently of each other. In Embodiment 4, no branch box 28 is interposed between the outdoor unit 2 and the indoor units 1a to 1 c.

In the air-conditioning apparatus 100C, the outdoor unit 2 is connected to the indoor units 1 by an extension pipe 10a, an extension pipe 10b, and an inter-unit communication line 27. In this state, when electric power is supplied to the air-conditioning apparatus 100C, communication automatically starts between the control board 21 of the outdoor unit 2 and the control boards 20 of the indoor units 1. Once the communication starts, the control board 21 of the outdoor unit 2 instructs the control boards 20 of the indoor units 1 to notify the control board 21 of the corresponding flammability classes CfL and installation height information.

The instructed control boards 20 of the indoor units 1 notify the control board 21 of the outdoor unit 2 of whether flammability classes CfL and installation height information are stored in the memory units 23 (memory units 23a to 23c) or not. When the flammability classes CfL and the installation height information are not stored, that is, the flammability classes CfL and the installation height information do not return, the control board 21 of the outdoor unit 2 inhibits operations of devices in the indoor unit 1 whose flammability class CfL and installation height information do not return, and displays an abnormality on at least one of the outdoor unit 2, the indoor unit 1, and the remote controller 26. In addition, the expansion valve 6 in the indoor unit 1 whose flammability class CfL and installation height information do not return is fully closed so that refrigerant does not flow.

When the flammability classes CfL and the installation height information are stored, the notified control board 21 of the outdoor unit 2 compares a flammability class CfS stored in the memory unit 25 and the flammability classes CfL. When at least one of the flammability class CfL satisfies the relationship of CfL<CfS, the control board 21 of the outdoor unit 2 inhibits operations of devices in the indoor unit 1 having this flammability class CfL, and displays an abnormality on at least one of the outdoor unit 2, the indoor unit 1, and the remote controller 26.

When all the flammability classes CfL satisfy the relationship of CfL≥CfS, the control board 21 of the outdoor unit 2 refers to the refrigerant amount information stored in the memory unit 25 of the outdoor unit 2 and the installation height information of the indoor units 1. When it is determined that there is the indoor unit 1 whose installation height is not satisfied, the control board 21 of the outdoor unit 2 inhibits operations of devices in the indoor unit 1 whose installation height is not satisfied, and displays an abnormality on at least one of the outdoor unit 2, the indoor unit 1, and the remote controller 26. In addition, the expansion valves 6 to which the indoor unit 1 whose installation height is not satisfied is connected is fully closed so that refrigerant does not flow.

On the other hand, the control board 21 of the outdoor unit 2 permits an air-conditioning operation of the indoor unit 1 whose installation height is satisfied, and does not display an abnormality.

When an air-conditioning operation is to be inhibited, it is desirable to inhibit an operation in an initial state of the air-conditioning apparatus 100B.

Embodiment 5

Figure 14:
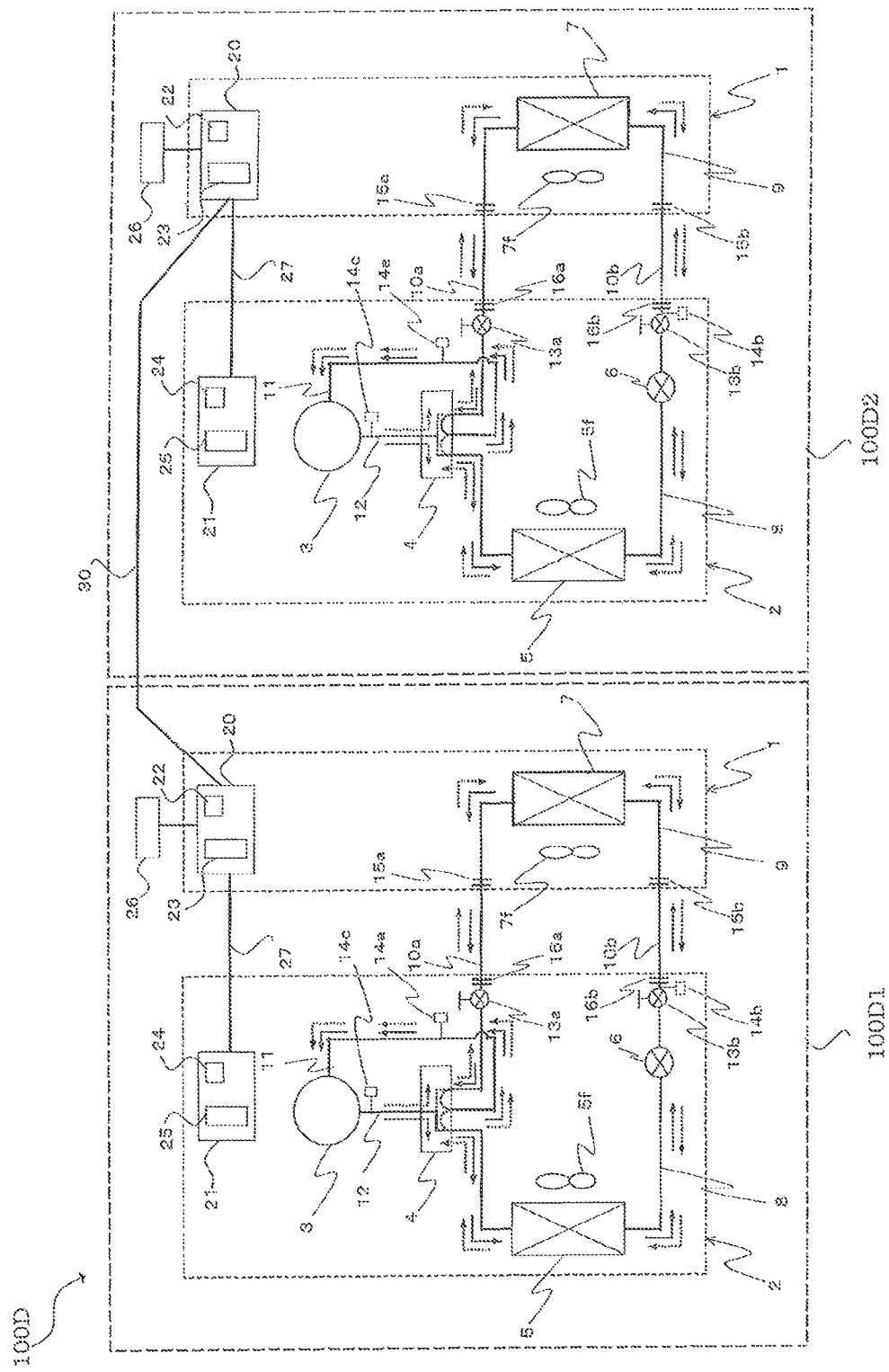
FIG. 14 schematically illustrates a refrigerant circuit configuration of an air-conditioning apparatus according to Embodiment 5 of the present invention.

FIG. 14 schematically illustrates a refrigerant circuit configuration of an air-conditioning apparatus 100D according to Embodiment 5 of the present invention. With reference to FIG. 14, a configuration and an operation of the air-conditioning apparatus 100D will be described. In Embodiment 5, in a manner similar to the description of the air-conditioning apparatus 100 according to Embodiment 1, the air-conditioning apparatus 100D used as a direct expansion air-conditioning system will be described. In Embodiment 5, the same reference signs designate the same parts in Embodiments 1 to 4, and aspects different from those of Embodiments 1 to 4 will be mainly described.

Embodiment 1 is directed to the air-conditioning apparatus 100 in which one indoor unit 1 is connected to one outdoor unit 2. On the other hand, Embodiment 5 is directed to the air-conditioning apparatus 100D in which an air-conditioning apparatus 100D1 and an air-conditioning apparatus 100D2 in each of which one indoor unit 1 is connected to one outdoor unit 2 are connected to each other by a system communication line 30 so that the air-conditioning apparatus 100D1 and the air-conditioning apparatus 100D2 operate at the same time. That is, the air-conditioning apparatus 100D includes a plurality of refrigerant systems. Configurations of the air-conditioning apparatus 100D1 and the air-conditioning apparatus 100D2 are similar to that of the air-conditioning apparatus 100 according to Embodiment 1.

In the air-conditioning apparatus 100D, a control board 20 of the indoor unit 1 of the air-conditioning apparatus 100D1 is connected to a control board 20 of the indoor unit 1 of the air-conditioning apparatus 100D2 by the system communication line 30. An apparatus number can be assigned to each of the air-conditioning apparatus 100D1 and the air-conditioning apparatus 100D2. Information on assigned apparatus number can be stored in at least one of the outdoor unit 2, the indoor unit 1, and the remote controller 26 in each of the air-conditioning apparatus 100D1 and the air-conditioning apparatus 100D2.

In the air-conditioning apparatus 100D, the outdoor unit 2 and the indoor unit 1 of the air-conditioning apparatus 100D1 are connected to each other by an extension pipe 10*a*, an extension pipe 10*b*, and an inter-unit communication line 27. The outdoor unit 2 and the indoor unit 1 of the air-conditioning apparatus 100D2 are connected to each other by an extension pipe 10*a*, an extension pipe 10*b*, and an inter-unit communication line 27. The control board 20 of the indoor unit 1 of the air-conditioning apparatus 100D1 is connected to the control board 20 of the indoor unit 1 of the air-conditioning apparatus 100D2 by the system communication line 30. In this state, when electric power is supplied to the air-conditioning apparatus 100D, communication automatically starts between the control board 21 of the outdoor unit 2 and the control board 20 of the indoor unit 1 in each of the air-conditioning apparatus 100D1 and the air-conditioning apparatus 100D2. Once the communication starts, the control board 21 of the outdoor unit 2 instructs the control board 20 of the indoor unit 1 to notify the control board 21 of the corresponding flammability class CfL and installation height information in each of the air-conditioning apparatus 100D1 and the air-conditioning apparatus 100D2.

In each of the air-conditioning apparatus 100D1 and the air-conditioning apparatus 100D2, the instructed control board 20 of the indoor unit 1 notifies the control board 21 of the outdoor unit 2 of whether a flammability class CfL and installation height information are stored in a memory unit 23 or not. When the flammability class CfL and the installation height information are not stored, that is, do not return, the control board 21 of the outdoor unit 2 inhibits operations of devices in the indoor unit 1 whose flammability class CfL and the installation height information do not return, and displays an abnormality on at least one of the outdoor unit 2, the indoor unit 1, and the remote controller 26.

When the flammability class CfL and the installation height information are stored, the notified control board 21 of the outdoor unit 2 compares a flammability class CfS stored in the memory unit 25 and the flammability class CfL. When the relationship of CfL<CfS is satisfied, the control board 21 of the outdoor unit 2 inhibits operations of devices in the indoor unit 1 having this flammability class CfL, and displays an abnormality on at least one of the outdoor unit 2, the indoor unit 1, and the remote controller 26.

When the relationship of CfL≥CfS is satisfied, the control board 21 of the outdoor unit 2 refers to the refrigerant amount information stored in the memory unit 25 of the outdoor unit 2 and the installation height information of the indoor unit 1. When it is determined that the installation height of the indoor unit 1 is not satisfied, the control board 21 of the outdoor unit 2 inhibits operations of devices in the indoor unit 1, and displays an abnormality on at least one of the outdoor unit 2, the indoor unit 1, and the remote controller 26. On the other hand, when it is determined that the installation height is satisfied, the control board 21 of the outdoor unit 2 permits an air-conditioning operation, and does not display an abnormality.

In the air-conditioning apparatus 100D, the use of the system communication line 30 enables notification of abnormality information to another air-conditioning apparatus. In this manner, another air-conditioning apparatus can display the apparatus number of the air-conditioning apparatus that has an abnormality in, for example, the remote controller 26 and abnormality information.

When an air-conditioning operation is to be inhibited, it is desirable to inhibit operations in initial states of the air-conditioning apparatus 100D1 and the air-conditioning apparatus 100D2.

In the foregoing description, Embodiments 1 to 5 of the present invention have been separately described; however, some of Embodiments 1 to 5 may be combined to constitute an appropriate air-conditioning apparatus. In this manner, features of some of Embodiments 1 to 5 are appropriately combined, and thus advantages of Embodiments 1 to 5 can be synergistically obtained.

In the examples of Embodiments 1 to 5, the flammability classes are compared, and then, the refrigerant amount information and the installation height information are referred. However, the air-conditioning apparatus of each of Embodiments 1 to 5 is assumed to use a flammable refrigerant, and thus the comparison of the flammability classes is not necessarily required, and it is only required that whether an air-conditioning operation is permitted or not is determined by referring to the maximum refrigerant amount and the installation height information. However, the comparison of the flammability classes enables inhibition of connection of an indoor unit 1 adapted only to specifications requiring lower degrees of safety than that of an outdoor unit 2, thus further contributing to safety.

In the examples of Embodiments 1 to 5, the installation height information of the indoor unit 1 is set appropriately to the configuration of the indoor unit 1. Alternatively, only the installation height of the indoor unit 1 may be set.

Embodiments 1 to 5 are based on an assumption that the control board 21 of the outdoor unit 2 is a main part of a control process. However, the present invention is not limited to this assumption, and the control board 20 of the indoor unit 1 or the branch box control board 29 of the branch box 28 may be a main part of the control process. Alternatively, the main part of the control process may be changed appropriately to cooperative control of the control board.

In the examples of Embodiments 1 to 4, the air-conditioning apparatus includes one outdoor unit 2. Alternatively, a plurality of outdoor units 2 may be provided so that the air-conditioning apparatus include outdoor units 2 parallelly connected to each other.

Similarly, in the air-conditioning apparatus 100D according to Embodiment 5, a plurality of outdoor units 2a may be connected and a plurality of outdoor units 2b may be connected in the air-conditioning apparatus 100D1 and the air-conditioning apparatus 100d2.

REFERENCE SIGNS LIST 1 indoor unit, 1a indoor unit, 1b indoor unit, 1c indoor unit, 2 outdoor unit, 2a outdoor unit, 2c outdoor unit, 3 compressor, 4 four-way valve, 5 outdoor heat exchanger, 5f outdoor fan, 6 expansion valve, 6a expansion valve, 6b expansion valve, 6c expansion valve, 7 indoor heat exchanger, 7a indoor heat exchanger, 7b indoor heat exchanger, 7c indoor heat exchanger, 7f indoor fan, 8 outdoor refrigerant pipe, 9 indoor refrigerant pipe, 10a extension pipe, 10b extension pipe, 11 suction pipe, 12 discharge pipe, 13a extension pipe connecting valve, 13b extension pipe connecting valve, 14a service port, 14b service port, 14c service port, 15a flare joint, 15b flare joint, 16a flare joint, 16b flare joint, 20 control board, 20a control board, 20b control board, 20c control board, 21 control board, 22 display unit, 23 memory unit, 23a memory unit, 23c memory unit, 24 display unit, 25 memory unit, 26 remote controller, 26a remote controller, 26b remote controller, 26c remote controller, 27 inter-unit communication line, 28 branch box, 29 branch box control board, 30 system communication line, 100 air-conditioning apparatus, 100A air-conditioning apparatus, 100B air-conditioning apparatus, 100C air-conditioning apparatus, 100D air-conditioning apparatus, 100D1 air-conditioning apparatus, 100D2 air-conditioning apparatus

The invention claimed is:

1. An air-conditioning apparatus comprising:
at least one outdoor unit; and
at least one indoor unit,
the air-conditioning apparatus circulating flammable refrigerant in the at least one outdoor unit and the at least one indoor unit,
the at least one outdoor unit including a compressor, a refrigerant path switching device, an outdoor heat exchanger, a pressure reducing device, an outdoor refrigerant pipe, and an outdoor control board, and storing refrigerant amount information concerning an amount of refrigerant enclosed in the at least one outdoor unit,
the at least one indoor unit including an indoor heat exchanger, an indoor refrigerant pipe, and an indoor control board, and storing installation height information concerning an installation height of the at least one indoor unit, and
the outdoor control board, in which information as to whether or not a concentration of flammable refrigerant reaches a flammable concentration range in an installation space of the indoor unit depending on the installation height of the indoor unit is set, being configured to, based on the refrigerant amount information and the installation height information:
permit an air-conditioning operation when the concentration of flammable refrigerant does not reach the flammable concentration range, and
inhibit the air-conditioning operation when the concentration of flammable refrigerant reaches the flammable concentration range.

2. The air-conditioning apparatus of claim 1, wherein:
the at least one outdoor unit further includes first information concerning a flammability of the flammable refrigerant usable in the at least one outdoor unit,
the at least one indoor unit further includes second information concerning a flammability of the flammable refrigerant usable in the at least one indoor unit, and
the outdoor control board compares the first information and the second information so that
when the outdoor control board determines that the flammable refrigerant usable in the at least one outdoor unit is more flammable than the flammable refrigerant usable in the at least one indoor unit, the outdoor control board inhibits the air-conditioning operation, and when the outdoor control board determines that the flammable refrigerant usable in the at least one outdoor unit is less flammable than the flammable refrigerant usable in the at least one indoor unit, the outdoor control board determines whether or not to permit the air-conditioning operation based on the refrigerant amount information and the installation height information.

3. The air-conditioning apparatus of claim 1, further comprising
a display unit displaying permission and inhibition of the air-conditioning operation.

4. The air-conditioning apparatus of claim 3, wherein
the display unit displays the refrigerant amount information and the installation height information.

5. The air-conditioning apparatus of claim 2, wherein
a display unit displays the first information and the second information.

6. The air-conditioning apparatus of claim 1, wherein:
the at least one indoor unit includes a plurality of indoor units, and
when the outdoor control board does not permit the air-conditioning operation of at least one of the plurality of indoor units, the outdoor control board inhibits the air-conditioning operation.

7. The air-conditioning apparatus of claim 1, wherein:
the at least one indoor unit includes a plurality of indoor units to which the flammable refrigerant is supplied at a time, and
the outdoor control board determines whether or not the air-conditioning operation is permitted for each of the plurality of indoor units.

8. The air-conditioning apparatus of claim 7, further comprising
a branch box disposed between the plurality of indoor units and the at least one outdoor unit and dividing the flammable refrigerant.

9. The air-conditioning apparatus of claim 1, wherein:
the at least one outdoor unit includes a plurality of outdoor units and the at least one indoor unit includes a plurality of indoor units to form a plurality of refrigerant systems, and
the outdoor control board determines whether or not the air-conditioning operation is permitted for each of the plurality of refrigerant systems.

10. The air-conditioning apparatus of claim 1, wherein:
the refrigerant amount information is stored in a memory unit provided in an outdoor unit control board, and
the installation height information is stored in a memory unit provided in an indoor unit control board.

11. The air-conditioning apparatus of claim 1, wherein R32 is used as the flammable refrigerant.

* * * * *